United States Patent [19]

Ohtani et al.

[11] Patent Number: 5,732,506
[45] Date of Patent: Mar. 31, 1998

[54] CULTIVATION OF PETUNIA

[75] Inventors: Toshio Ohtani; Naoya Fukuda; Sadanori Sase; Limi Okushima, all of Ibaraki, Japan

[73] Assignee: National Research Institute of Agricultural Engineering, Ministry of Agriculture, Forestry and Fisheries, Ibaraki, Japan

[21] Appl. No.: 626,968

[22] Filed: Apr. 3, 1996

[51] Int. Cl.$^6$ ...................................................... A01H 3/02
[52] U.S. Cl. ............................................ 47/58; 47/DIG. 6
[58] Field of Search ................................ 47/58, DIG. 6

[56] References Cited

U.S. PATENT DOCUMENTS 4,788,793  12/1988  Kadkade ...................................... 47/58

FOREIGN PATENT DOCUMENTS 04349823  12/1992  Japan.

OTHER PUBLICATIONS

Scientia Horticulturea, vol. 48, pp. 141–151, 1991, Roar Moe $^a$, et al. "Stem Elongation and Flowering of The Long–Day Plant Campanula Isophylla Moretti in Response to Day and Night Temperature Alternations and Light Quality".

Scientia horticulutrae, vol. 45, pp. 345–351, 1991, Maigull Appelgren, "Effects of Light Quality on Stem Elongation of Pelargonium in Vitro".

J. Amer. Soc. Hort. Sci., vol. 117, No. 3, pp. 481–485, 1992, Nihal C. Rajapakse, et al., "Regulation of Chrysanthemum Growth by Spectral Filters".

Krol et al. Antisense chalcone synthase genes in petunia: visualization of variable transgene expression. Molecular and General Genetics. vol. 220. PP. 204–212.

Weiss et al. the role of light reactions in the regulation of anthocyanin synthesis in Petunia corollas. Physiologia Plantarum. vol. 81. pp. 127–133.

De Graaf et al, The Effect of Dy Extensions with Different Light Qualities on The Morphogenesis of Fuchsia, Petunia and Pelargonium. Acta Horticulurae, vol. 305, 1992, pp. 85–94.

*Primary Examiner*—Douglas W. Robinson
*Assistant Examiner*—Melissa L. Kimball
*Attorney, Agent, or Firm*—Oblon, Spivak, McClelland, Maier & Neustadt, P.C.

[57] ABSTRACT

To make it possible to control the external view of flowers of petunias not by breeding but by only controlling cultivation environment, a method of cultivating a petunia having a colored portion and an outer margin in its corolla is proposed, which comprises controlling light quality of cultivation light in the daylight period after a seedling culture stage, in particular, after flower-bud differentiation until blooming to thereby control the proportion of the colored portion to the outer margin in the corolla. Especially, to broaden the outer margin in the corolla of the petunia, it is preferable to use yellow light as the cultivation light, and to narrow it, blue light as the light quality.

8 Claims, 1 Drawing Sheet

5,732,506

CULTIVATION OF PETUNIA

BACKGROUND OF THE INVENTION

1. Field of the Invention

This invention relates to a method of cultivating petunias. More particularly, this invention relates to a method of cultivating petunias that controls the proportion of colored portions to outer margins in corollas of petunias by controlling light quality of cultivating light.

2. Description of the Related Art

Petunias have a long flowering season, and bloom one after another from spring to autumn. Hence, they are widely cultivated for use in ornamental flowering plants put in flower beds, verandas or porches, table flower pots and so forth.

Petunia have very many phyletic lines and varieties, and those with various external views are available. For example, those having colored portions and outer margins in corollas and those having monochromatic corollas are available. They have also a great variety in the color of corollas and the distribution of flower colors. In ornamental flowering plants, however, those having much more various external views are called for in respect of the color of corollas and the distribution of flower colors so that they can suit various tastes of those who admire flowers. Accordingly, plant breeding is being repeated by mating, selection, genetic recombination and so forth.

The plant breeding achieved by mating, selection or genetic recombination, however, requires much labor and time and it is not easy to achieve the intended results. Hence, it has been sought to develop a new method so that the external view of flowers can be more easily controlled.

SUMMARY OF THE INVENTION

An object of the present invention is to make it possible to control the external view of flowers of petunias not by breeding but by only controlling cultivation environment.

The present inventors have discovered that, in the cultivation of a petunia having a colored portion and an outer margin in its corolla, the proportion of the colored portion to the outer margin in the corolla can be changed by controlling light quality of cultivation light, whereby the above object can be achieved. Thus, they have accomplished the present invention.

More specifically, the present invention provides a method of cultivating a petunia having a colored portion and an outer margin in its corolla, the method comprising controlling light quality of cultivation light in the daylight period after a seedling culture stage, in particular, after flower-bud differentiation until blooming to thereby control the proportion of the colored portion to the outer margin in the corolla.

As particularly preferred embodiments, the present invention provides, in the cultivation of a petunia, a method wherein yellow light is used as the cultivation light to thereby broaden the outer margin in the corolla, or a method wherein blue light is used as the cultivation light to thereby narrow the outer margin in the corolla.

DETAILED DESCRIPTION OF THE INVENTION

In the present invention, the petunia includes various petunias so long as they have a colored portion and an outer margin in the corolla. There are no particular limitations on their phyletic lines and varieties.

Figure 2:
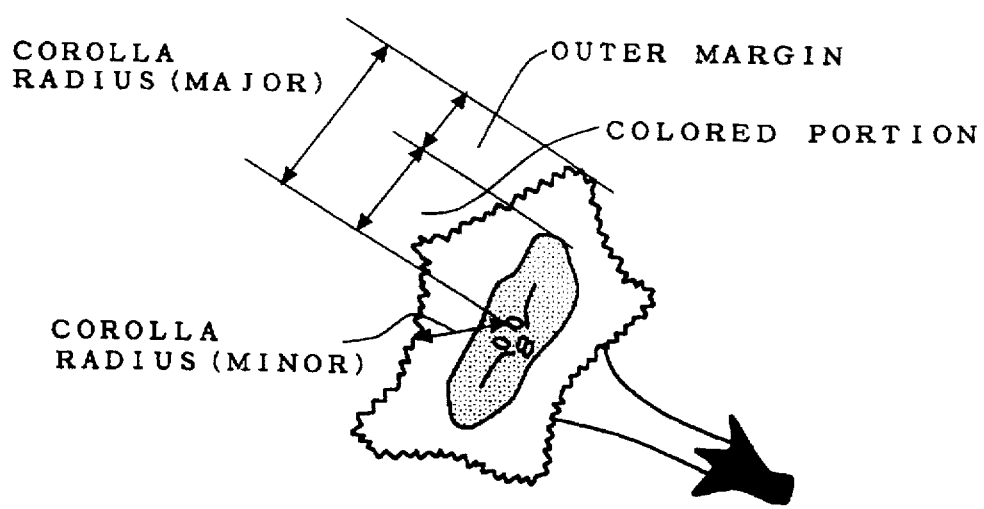
FIG. 2 is a view to illustrate the terms relating to the form of flower of a petunia.

In the present invention, among the terms relating to the form of flower of petunias, the portions respectively meant by "outer margin", "colored portion", "corolla radius (major)" and "corolla radius (minor)" are as shown in FIG. 2.

In the cultivation method of the present invention, the light quality of cultivation light, stated more specifically, the wavelength distribution of cultivation light, used when a petunia having a colored portion and an outer margin in its corolla is cultivated is controlled to thereby control the proportion of the colored portion to the outer margin in the corolla.

Here, as manners for controlling the wavelength distribution of cultivation light, it is meant to use light of the wavelength region assorted for each color such as white color, red color, yellow color, green color or blue color. The wavelength distribution of cultivation light of each color, however, is by no means so strict as to exclude the light of the wavelength regions of different colors. The present invention can be effective so long as the middle of energy distribution of cultivation light is within the region of each color. For example, five kinds of light quality as shown in Table 1 can be obtained when metal halide lamps of respective colors are used as light sources. In the present invention, the light quality of cultivation light can be controlled using the light assorted in this way.

TABLE 1

| | Wavelength Distribution of Cultivation Light (percentages to total amount of light) | | | | | | |
|---|---|---|---|---|---|---|---|
| Wavelength (nm): | UV-A 300–400 | Blue 400–500 | Green 500–550 | Yellow 550–600 | Red 600–700 | Near infrared 700–750 | Infrared >750 |
| Light quality of cultivation light: | | | | | | | |
| White light: | 2.25 | 9.67 | 5.69 | 10.41 | 15.31 | 10.00 | 48.35 |
| Red light: | 1.80 | 6.77 | 2.68 | 21.41 | 32.62 | 4.60 | 31.35 |
| Yellow light: | 0.35 | 3.17 | 0.36 | 47.06 | 5.85 | 1.11 | 42.34 |
| Green light: | 7.43 | 9.07 | 33.95 | 5.49 | 6.68 | 3.70 | 34.22 |
| Blue light: | 6.15 | 40.88 | 5.84 | 6.68 | 5.18 | 3.62 | 34.13 |

What cultivation light be used among the groups of cultivation light with such light quality may be appropriately determined in accordance with the lines and varieties of petunias or the desired proportion of the colored portions to the outer margins in corollas.

For example, when the outer margins of petunias are made broader than the colored portions thereof, yellow light is used. On the other hand, when the outer margins are made narrower, blue light is used.

In the present invention, the time to start the cultivation under light having the specific light quality as shown above, and the period for such cultivation may be appropriately determined in accordance with the lines and varieties of the petunias, the degree of controlling the proportion of the colored portions to the outer margins in corollas, the intensity of light, and so forth. Such cultivation may be carried out at least after a seedling culture stage, and irradiation with the light having specific light quality need not be made in a seed stage or germinal stage. In usual cases, the irradiation with the light having specific light quality may be made in the cultivation period from flower-bud differentiation until blooming, whereby a flower of a petunia observed as a different variety from its external view can be obtained.

With regard to individual flowers, it is unnecessary to continue irradiation with the light having specific light quality, after flower buds have opened. As the whole plant, however, it is preferable to control the light quality throughout the flowering period of that plant in order to control the proportions of colored portions to outer margins of the corollas of all the flowers blooming one after another. If the control of light quality is stopped in the flowering period, it follows that flowers having the same flower color distribution as the case where the light quality is not controlled may bloom from flower buds formed thereafter on that plant. On the other hand, when flowers having different flower color distribution are made to bloom on the same plant, it is preferable to stop the control of light quality.

The time for which the petunias are irradiated with the cultivation light a day during the cultivation may be the same as that in conventional cultivation methods. It is unnecessary to make the irradiation all day. The irradiation time may be appropriately determined in accordance with the desired flowering time and so forth.

In the present invention, the same procedure as in conventional cultivation methods may be used except for the control of light quality of cultivation light.

EXAMPLES

The present invention will be described below in greater detail by giving Example.

Example 1

Seedling-cultured petunias (name of variety: Baccarat Blue Picotee; colored portions of corollas: blue; outer margins: white) were cultivated in the following way over a period of 6 weeks from August 18th and on five plants per cultivation light with different kind of light quality.

More specifically, the seedling-cultured petunias were transplanted to plastic bottles, which were then set on the bottoms of growth chambers. At the upper part in each growth chamber, a metal halide lamp was provided as a light source and its ultraviolet rays were shielded by an acrylic plate. Light sources with five kinds of light quality as previously shown in Table 1 were used as cultivation light sources. In this instance, the height of each light source was adjusted so that the light intensity of cultivation light was 400 $\mu mol \cdot m^{-2} \cdot s^{-1}$ at the top of the plant. The length of a day was divided into 12 hours for the light and dark periods each.

During the cultivation, the flower's dimensions [corolla radius (major), corolla radius (minor), and breadth of outer margin] and dry weight were measured at intervals of a week.

Figure 1:
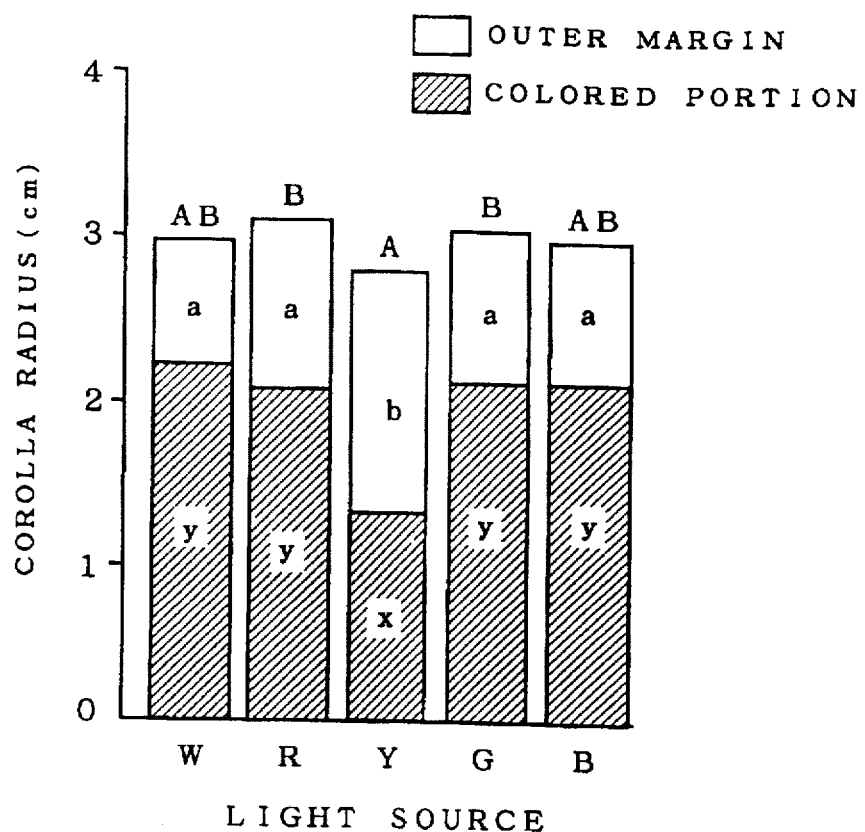
FIG. 1 shows the relationship between the light quality of cultivation light for petunias, the corolla radius and the proportion of the breadth of an outer margin held therein.

The results of measurement are shown in FIG. 1 in respect of a corolla radius and the proportion of the breadth of an outer margin held therein, of each flower having bloomed 30 days after the cultivation in growth chambers. In FIG. 1, the alphabetic letter symbols show that there are significant differences at a level of 5% according to the Duncan's multiple test, between values (represented by columns) marked with different letters among the respective group of AB, A and B (indicating values of corolla radii), group of a and b (values of outer margins) and group of x and y (values of colored portions).

As is seen from FIG. 1, the outer margins of corollas have become broader than the colored portions as a result of the cultivation under yellow light containing the light with a wavelength of 400 to 500 nm in a smaller proportion. In external views, these petunias were observed as those having distribution of flower colors different from one another. In this instance, there was no difference in the total dry weight of leaves, flowers, stems and roots between those cultivated under yellow light and those cultivated under other light. Thus, it can be confirmed that the plants were in normal growth.

As described above, according to the present invention, the light quality of cultivation light is controlled in the cultivation of petunias to thereby control the proportion of the colored portion to the outer margin in the corolla. Hence, it is possible to control the external view of the flowers of petunias without relying on breeding.

What is claimed is:

1. A method of cultivating a plant of the genus Petunia having a colored portion and a non-colored outer margin in the corolla thereof so as to broaden the non-colored outer margin of the corolla, the method comprising cultivating the plant under yellow light as a cultivation light after a seedling stage thereof.

2. The method of claim 1, wherein the yellow light is used as the cultivation light throughout the flowering period of the petunia.

3. The method of claim 1, wherein the yellow light is used for less than the entire flowering period of the petunia.

4. The method of claim 1, wherein the yellow light is used as a cultivation light after flower bud differentiation.

5. The method of claim 4, wherein the yellow light is used as the cultivation light throughout the flowering period of the petunia.

6. The method of claim 1, wherein said yellow light has 47.06% of said total light in the range of 550 to 600 nm.

7. The method of claim 1, wherein said yellow light has an intensity of 400 $\mu mol \cdot m^{-2} \cdot s^{-1}$ at the top of the plant.

8. The method of claim 1, wherein said plant is the variety Baccarat Blue Picotee.

* * * * *

UNITED STATES PATENT AND TRADEMARK OFFICE
CERTIFICATE OF CORRECTION

PATENT NO. : 5,732,506
DATED : March 31, 1998
INVENTOR(S) : Toshio OHTANI, et al.

It is certified that error appears in the above-identified patent and that said Letters Patent is hereby corrected as shown below:

Column 1, line 17, "Petunia" should read --Petunias--.

Column 2, line 34, "is cultivated is"should read --is cultivated and--.

Column 3, line 1, "be used" should read --may be used--.

Signed and Sealed this

Twenty-seventh Day of October, 1998

Attest:

BRUCE LEHMAN

*Attesting Officer*      *Commissioner of Patents and Trademarks*